United States Patent [19]

Kust et al.

[11] Patent Number: 4,509,973
[45] Date of Patent: Apr. 9, 1985

[54] PLANT GROWTH REGULATING COMPOSITIONS

[75] Inventors: Cyril Kust, Pennington; Prithvi Bhalla, Hightstown, both of N.J.

[73] Assignee: American Cyanamid Company, Stamford, Conn.

[21] Appl. No.: 570,568

[22] Filed: Jan. 13, 1984

[51] Int. Cl.³ ............................................ D01N 43/50
[52] U.S. Cl. ............................................ 71/92; 71/121
[58] Field of Search ............................... 71/92, 121

[56] References Cited

PUBLICATIONS

Orwick et al., European Pat. Appl. EP 41,624, Chem. Abst. vol. 97, (1982) 105607j.

Primary Examiner—Catherine L. Mills
Attorney, Agent, or Firm—Estelle J. Tsevdos; Alphonse R. Noë

[57] ABSTRACT

The present invention relates to plant growth regulating compositions comprising the mixtures of (2-chloroethyl)-trimethylammonium chloride and 2-(4-isopropyl-4-methyl-5-oxo-2-imidazolin-2-yl) 3-quinolinecarboxylic acid, as active ingredients. These compositions enhance crop yields of wheat or barley.

8 Claims, No Drawings

PLANT GROWTH REGULATING COMPOSITIONS

BACKGROUND OF THE INVENTION

The present invention relates to plant growth regulating compositions containing (2-chloroethyl)trimethylammonium chloride and 2-(4-isopropyl-4-methyl-5-oxo-2-imidazolin-2-yl) 3-quinoline carboxylic acid, as the active ingredients. Compositions containing these active ingredients enhance yields of such crops as wheat and barley.

Plant growth regulating methods utilizing (2-chloroethyl)-trimethylammonium chloride, as the active ingredient, are disclosed in U.S. Pat. No. 3,156,554, Tolbert, issued Nov. 10, 1964. Furthermore, compositions containing chlorocholine and a choline salt, in ratios of 1:0.05 to 1:20, used in controlling stem growth in plants, are disclosed in U.S. Pat. No. 3,395,009, Oettel, et al, issued July 30, 1963.

The use of the other active ingredient of the present invention, 2-(4-isopropyl-4-methyl-5-oxo-2-imidazolin-2-yl)-3-quinolinecarboxylic acids, as a plant-growth regulant, is disclosed in European Patent Application No. 41,624, Orwick et al. The types of plant growth regulating activities suggested in that application include increases in axillary branching, tillering, flowering and increases in yields of agronomic and horticultural crops.

However, the above-discussed references do not disclose or suggest combining both of the active ingredients of the present invention, and even more so, these references fail to disclose that the compositions of the present invention increase yields of such crops as wheat and barley. This enhancement of crop yield is above and beyond that observed when each compound alone is applied to such crops as wheat and/or barley. And therefore, the compositions of the present invention provide beneficial and unexpected crop yield results.

It is an object of the present invention, therefore, to provide plant growth regulating compositions which enhance crop yields.

It is a further object of this invention to increase crop yields in such crops as wheat and barley.

These and other objects of the present invention will become apparent by the following more detailed description of the invention.

DESCRIPTION OF THE INVENTION

The present invention relates to plant growth regulating compositions comprising, as the active ingredients, (2-chloroethyl)-trimethylammonium chloride and 2-(4-isopropyl-4-methyl-5-oxo-2-imidazolin-2-yl)-3-quinoline carboxylic acid. These compositions are aqueous solutions such that about 920 to 1610 g/ha of (2-chloroethyl)trimethylammonium chloride are delivered to crops, as well as about 0.5 to 4 g/ha of 2-(4-isopropyl-4-methyl-5-oxo-2-imidazolin-2-yl)-3-quinolinecarboxylic acid is provided to crops.

While the plant growth regulating compositions of the present invention are comprised of the above-described essential components, certain other adjuvant components also may be present in the compositions. For instance, it is recognized by those familiar in the art that surfactants are commonly used in the formulation of agricultural preparations. Suitable surfactants useful in the compositions of the present invention include nonionic surfactants, about 0.10% to 5.0% in final preparation.

The nonionic surfactants suitable for use in the present compositions include those well-known to those skilled in the art. Suitable such surfactants include dialkylphenoxypoly(ethyleneoxy) alcohols, polysorbate sorbitan mononoleates, among others.

In addition to nonionic surfactants, the present plant growth regulating composition may also contain other minor adjuvants such as alcohols ($C_1$-$C_4$ or benzyl alcohols) at levels of 0% to 5% of final formulation.

In preparing these compositions commercially-available aqueous formulations of (2-chloroethyl)-trimethylammonium chloride, which may contain about 0% to 32% choline chloride, on a weight volume basis, in amounts to provide about 920 to 1610 grams of active ingredient per hectare, are admixed in a spray tank with an aqueous solution of 2-(4-isopropyl-4-methyl-5-oxo-1-imidazolin-2-yl) 3-quinolinecarboxylic acid, in amounts to provide about 0.5 to 4 grams of active ingredient per hectare. The thus-formed mixture is then diluted with enough water to provide a volume, whereby about 100 to 400 liters of composition per hectare is applied.

The present invention is further illustrated by the following non-limiting examples.

EXAMPLES 1–12

Plant growth regulating compositions comprising aqueous combinations of (A) (2-chloroethyl)-trimethylammonium chloride and (B) 2-(4-isopropyl-4-methyl-5-oxo-2-imidazolin-2-yl) 3-quinolinecarboxylic acid An aqueous solution containing 2-(4-isopropyl-4-methyl-5-oxo-2-imidazolin-2-yl)3-quinolinecarboxylic acid (12.44 g, 88.42% pure) and isopropylamine (2.83 g) in 11 liters of water to provide the equivalent of from 0.5 to 4 grams per hectare of the 3-quinolinecarboxylic acid, is added to a spray tank containing a 46% aqueous solution of (2-chloroethyl)trimethylammonium chloride containing choline chloride to provide the equivalent of from 920 to 1610 grams per hectare of this active ingredient. Water is then added to provide a total spray volume of from 100 to 400 liters per hectare.

The thus-prepared aqueous combinations are applied to field plots of several varieties of wheat and barley. Crop yields at harvest are obtained and reported in metric tons per hectare in Table I and Table II.

TABLE I

| | | Wheat | | | | |
|---|---|---|---|---|---|---|
| Number | Variety | A g/ha | B g/ha | Yield mt/ha | % Yield increase | % Increase yield over the sum of the individual effects |
| 1 | Fidel | — | — | 7.11 | — | — |
| | | 920.0 | — | 7.22 | 1.55 | — |
| | | — | 1.0 | 7.00 | −1.55 | — |
| | | — | 2.0 | 7.16 | 0.70 | — |
| | | 920.0 | 0.5 | 7.51 | 5.63 | 5.66 |
| | | 920.0 | 1.0 | 7.50 | 5.49 | 5.49 |
| | | 920.0 | 2.0 | 7.61 | 7.03 | 4.78 |
| | | 920.0 | 4.0 | 7.49 | 5.34 | — |
| 2 | Lario | — | — | 7.43 | — | — |
| | | 1380.0 | — | 7.95 | 7.00 | — |
| | | — | 1.0 | 8.02 | 7.94 | — |
| | | 1380.0 | 1.0 | 8.87 | 19.38 | 4.44 |
| 3 | Argelato | — | — | 6.64 | — | — |
| | | 1380.0 | — | 6.96 | 4.82 | — |
| | | — | 1.0 | 6.78 | 2.11 | — |
| | | 1380.0 | 0.5 | 7.44 | 12.05 | 5.12 |
| | | 1380.0 | 1.0 | 7.43 | 11.90 | 4.97 |
| 4 | Long- | — | — | 8.79 | — | — |

TABLE I-continued

Wheat

| Number | Variety | A g/ha | B g/ha | Yield mt/ha | % Yield increase | % Increase yield over the sum of the individual effects |
|---|---|---|---|---|---|---|
| | bow | 1130.0 | — | 8.77 | −0.23 | — |
| | | — | 2.0 | 8.84 | 0.57 | — |
| | | 1130.0 | 2.0 | 9.11 | 3.64 | 3.3 |
| 5 | Norman | — | — | 7.09 | — | — |
| | | 1130.0 | — | 6.92 | −0.24 | — |
| | | — | 1.0 | 7.13 | 0.56 | — |
| | | 1130.0 | 1.0 | 7.29 | 2.82 | 2.5 |

TABLE II

Barley

| Number | Variety | A g/ha | B g/ha | Yield mt/ha | % Yield increase | % Increase yield over the sum of the individual effects |
|---|---|---|---|---|---|---|
| 6 | Capri | — | — | 6.37 | — | — |
| | | 1380.0 | — | 6.32 | −0.79 | — |
| | | — | 2.0 | 6.39 | 0.31 | — |
| | | 1380.0 | 2.0 | 6.80 | 6.75 | 7.22 |
| | | 1380.0 | 4.0 | 6.58 | 3.30 | — |
| 7 | Sonja | — | — | 5.35 | — | — |
| | | 1380.0 | — | 5.28 | −1.31 | — |
| | | — | 2.0 | 5.45 | 1.87 | — |
| | | 1380.0 | 2.0 | 5.77 | 7.85 | 7.29 |
| 8 | Gerbel | — | — | 5.96 | — | — |
| | | 1380.0 | — | 6.29 | 5.54 | — |
| | | — | 2.0 | 5.94 | −0.34 | — |
| | | 1380.0 | 2.0 | 6.41 | 7.72 | 2.52 |
| 9 | Maris Otter | — | — | 5.94 | — | — |
| | | 1610.0 | — | 6.06 | 2.02 | — |
| | | — | 1.0 | 6.21 | 4.55 | — |
| | | — | 2.0 | 5.97 | 0.51 | — |
| | | 1610.0 | 0.5 | 6.38 | 7.41 | 0.84 |
| | | 1610.0 | 2.0 | 6.26 | 5.39 | 2.86 |
| | | 1610.0 | 4.0 | 6.32 | 6.40 | — |
| 10 | Mammut | — | — | 6.41 | — | — |
| | | 1380.0 | — | 6.57 | 2.50 | — |
| | | — | 1.0 | 6.21 | −3.12 | — |
| | | — | 2.0 | 6.17 | −3.74 | — |
| | | 1380.0 | 0.5 | 6.52 | 1.72 | ~3.80 |
| | | 1380.0 | 1.0 | 6.62 | 3.28 | 3.90 |
| | | 1380.0 | 2.0 | 6.74 | 5.15 | 6.40 |
| | | 1380.0 | 4.0 | 6.64 | 3.59 | — |
| 11 | Menuet | — | — | 4.48 | — | — |
| | | 1380.0 | — | 4.85 | 8.26 | — |
| | | — | 2.0 | 4.50 | 0.45 | — |
| | | 1380.0 | 2.0 | 4.97 | 10.94 | 2.23 |
| 12 | Triumph | — | — | 3.34 | — | — |
| | | 1610.0 | — | 3.43 | 2.69 | — |
| | | — | 1.0 | 3.40 | 1.80 | — |
| | | — | 2.0 | 3.57 | 6.89 | — |
| | | 1610.0 | 1.0 | 3.69 | 10.48 | 5.99 |
| | | 1610.0 | 4.0 | 3.71 | 11.08 | — |
| | | 1610.0 | 1.0 | 3.68 | 10.18 | 5.69 |
| | | 1610.0 | 2.0 | 3.71 | 11.08 | 1.50 |

What is claimed is:

1. A plant growth regulating composition for use on a crop, said composition comprising: (2-chloroethyl)-trimethylammonium chloride and 2-(4-isopropyl-4-methyl(5-oxo-2-imidazolin-2-yl) 3-quinolinecarboxylic acid, as the active ingredients; wherein said (2-chloroethyl)trimethylammonium chloride and said 2-(4-isopropyl-4-methyl(5-oxo-2-imidazolin-2-yl) 3-quinolinecarboxylic acid are present in the ratio of about 3220:1 to 230:1 as provided to said crop.

2. A plant growth regulating composition according to claim 1, wherein said composition is an aqueous solution.

3. A plant growth regulating composition according to claim 2, wherein about 100 to 400 liters per hectare of water containing said composition, provides about 920 to 1610 grams per hectare of said (2-chloroethyl)triethylammonium chloride and about 0.5 to 4.0 grams per hectare of said 2-(4-isopropyl-4-methyl-5-oxo-2-imidazolin-2-yl) 3-quinolinecarboxylic acid to said crop.

4. A plant growth regulating composition according to claim 3, wherein said crop is wheat or barley.

5. A method for increasing the yield of a crop, said method comprising: applying to said crop, a crop-yield-enhancing amount of a composition containing, as active ingredients, (2-chloroethyl)-trimethylammonium chloride and 2-(4-isopropyl-4-methyl-5-oxo-2-imidazolin-2-yl)3-quinolinecarboxylic acid; wherein said (2-chloroethyl)-trimethylammonium chloride and said 2-(4-isopropyl-4-methyl-5-oxo-2-imidazolin-2-yl) 3-quinolinecarboxylic are present in the ratio of about 3220:1 to 230:1 as provided to said crop.

6. A method according to claim 5, wherein said composition is an aqueous solution.

7. A method according to claim 6, wherein about 100 to 400 liters per hectare of water containing said composition, said method providing about 920 to 1610 grams per hectare of said (2-chloroethyl)-trimethylammonium chloride and about 0.5 to 4.0 of said 2-(4-isopropyl-4-methyl-5-oxo-2-imidazolin-2-yl) 3-quinolinecarboxylic acid to said crop.

8. A method according to claim 1, wherein said crop is wheat or barley.

* * * * *